(12) United States Patent
Matsuba et al.

(10) Patent No.: US 6,492,528 B1
(45) Date of Patent: Dec. 10, 2002

(54) 1,3-DIALKYL-2-IMIDAZOLIDINONES AND A MANUFACTURING PROCESS THEREFOR

(75) Inventors: Katsuhiko Matsuba, Kanagawa (JP); Shinichi Nakagawa, Kanagawa (JP); Takazou Katou, Kanagawa (JP); Yoshihiro Yamamoto, Kanagawa (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 09/414,513

(22) Filed: Oct. 8, 1999

(30) Foreign Application Priority Data

| Oct. 9, 1998 | (JP) | 10-288448 |
| Oct. 9, 1998 | (JP) | 10-288449 |
| Oct. 15, 1998 | (JP) | 10-294280 |

(51) Int. Cl.$^7$ .......................................... C07D 233/04
(52) U.S. Cl. .................................................. 548/316.4
(58) Field of Search .................................. 548/316.4

(56) References Cited

U.S. PATENT DOCUMENTS

| 2,892,843 A | | 6/1959 | Levine | 260/309.7 |
| 4,617,400 A | * | 10/1986 | Ito et al. | 548/316.4 |
| 4,668,793 A | * | 5/1987 | Nagata et al. | 548/316.4 |
| 4,731,453 A | * | 3/1988 | Nagata et al. | 548/316.4 |
| 4,864,026 A | * | 9/1989 | Bickert et al. | 544/315 |
| 4,897,480 A | * | 1/1990 | Schoenleben | 544/315 |
| 4,918,186 A | * | 4/1990 | Kajimoto et al. | 540/492 |
| 4,925,940 A | * | 5/1990 | Franz et al. | 544/315 |
| 4,970,321 A | * | 11/1990 | Betz et al. | 548/316.4 |
| 5,011,936 A | * | 4/1991 | Kobayashi et al. | 548/316.4 |
| 5,594,149 A | * | 1/1997 | Naruse et al. | 548/316.4 |

FOREIGN PATENT DOCUMENTS

| EP | 0 823 427 | | 2/1998 | |
| JP | 53-111062 | * | 9/1973 | 548/316.4 |
| JP | 53-73561 | | 6/1978 | |
| JP | 57-98268 | | 6/1982 | |
| JP | 57-120570 | | 7/1982 | |
| JP | 57-175170 | | 10/1982 | |
| JP | 59-155364 | | 9/1984 | |
| JP | 60-3299 | | 1/1985 | |
| JP | 60-243071 | | 12/1985 | |
| JP | 61-109772 | | 5/1986 | |
| JP | 61-172862 | | 8/1986 | |
| JP | 61-229866 | | 10/1986 | |
| JP | 61-233674 | | 10/1986 | |
| WO | WO96/02516 | | 2/1996 | |

OTHER PUBLICATIONS

"Ruthenium catalyzed reactions of ethylene glycol with primary amines: steric factors and selectivity control", *Journal of Organometallic Chemistry,* 407 pp. 97–105 (1991).

Chemical Abstracts, vol. 129, No. 14, Oct. 5, 1998, abstract No. 175642v, p. 670; XP002126318 and JP 10 226679, Aug. 25, 1998.

Chemical Abstracts, vol. 97, No. 25, Dec. 20, 1982, abstract No. 216180j, p. 854; XP002126319 and JP 57 098268, Jun. 18, 1982.

Chemical Abstracts, vol. 102, No. 11, Mar. 18, 1985, abstract No. 95641w, p. 576; XP002126320 and JP 59 155364.

* cited by examiner

*Primary Examiner*—Floyd D Higel
*Assistant Examiner*—Kamal Saeed
(74) *Attorney, Agent, or Firm*—Burns Doane Swecker & Mathis LLP

(57) ABSTRACT

This invention provides a convenient process for manufacturing 1,3-dialkyl-2-imidazolidinones in a direct one-step reaction from industrially available alkylene carbonate, N-alkylethanolamine or 1,2-diol, which can minimize forming solid materials and be readily conducted in an industrial large-scale production with a higher yield and less byproducts. The process is characterized in that alkylene carbonate, N-alkylethanolamine or 1,2-diol is reacted with monoalkylamine and carbon dioxide, alkylcarbamate alkylamine salt, and/or 1,3-dialkylurea, by heating them at 50° C. or higher in a reactor whose area in contact with at least part of the reactants and/or products is made of a metal comprising titanium or zirconium and/or an oxide thereof or inorganic glass.

40 Claims, No Drawings

1,3-DIALKYL-2-IMIDAZOLIDINONES AND A MANUFACTURING PROCESS THEREFOR

BACKGROUND OF THE INVENTION

1. Field of the Invention

This invention relates to 1,3-dialkyl-2-imidazolidinones and a manufacturing process therefor.

1,3-Dialkyl-2-imidazolidinones have been extensively used as, for example, an aprotic polar solvent; for example, they are useful as a solvent for a resin such as polyamide, polystyrene, polyester, polyvinyl chloride or a phenol resin; a reaction solvent for various kinds of organic syntheses; or an extraction solvent for extracting an aromatic hydrocarbon from an aliphatic hydrocarbon. Among 1,3-dialkyl-2-imidazolidinones, 1,3-dimethyl-2-imidazolidinone (hereinafter, referred to as "IDMI") is particularly useful because it is remarkably resistant to a strong base, is little decomposed when heated with a solution of an alkali-metal hydroxide, and therefore, is suitably used as a reaction solvent for dehalogenation of an aromatic organic halide, in particular polychlorobiphenyls.

2. Description of the Prior Art

Various preparation processes for 1,3-dialkyl-2-imidazolidinones have been suggested, in which N,N'-dialkylethylenediamine is involved as a starting material; for example, reacting N,N'-dimethylethylenediamine with trichloromethyl chloroformate as disclosed in JP-A 53-73561; reacting N,N'-dimethylethylenediamine with carbon dioxide as disclosed in JP-A 57-175170; reacting N,N'-dialkylethylenediamine with phosgene in the presence of water and dehydrochlorinating agent as disclosed in JP-As 61-109772 and 61-172862; reacting N,N'-dimethylethylenediamine with urea in the presence of a polar solvent as disclosed in JP-A 7-252230. As the starting material, N,N'-dimethylethylenediamine can be prepared by a well-known process, in which ethylene dichloride and monomethylamine are reacted as described in JP-A 57-120570. The process involves a problem of disposing a large amount of byproduct, sodium chloride contaminated by organic compounds. A reaction of ethylene glycol with monomethylamine in the presence of a homogeneous catalyst consisting of ruthenium and triphenylphosphine has been suggested to prepare N,N'-dimethylethylenediamine as disclosed in J.Organometallic Chem., Vol.407, p.97 (1991). It is, however, difficult to industrially recover and recycle such a homogeneous precious metal catalyst. Thus, it cannot be said to be ideal to produce 1,3-dialkyl-2-imidazolidinone from N,N'-dialkylethylenediamine.

There have been suggested a reductive addition of 2-imidazolidinone and formaldehyde in the presence of a hydrogenating catalyst (JP-A 60-243071) and a catalytic reduction of dialkyl ether of N,N'-hydroxymethylimidazolidinone (JP-B 60-3299) as another attempt to prepare N,N'-dialkylimidazolinones. These also involve the above problem because a starting material is prepared from dimethylethylenediamine, and are impractical because its processes are lengthy.

There have been disclosed interesting processes, i.e., reactions of N-alkylmonoethanolamine with an alkylamine such as monomethylamine, and with carbon dioxide, alkylcarbamate alkylamine salt or 1,3-dialkylurea (JP-A 57-98268); a reaction of ethylene glycol with carbon dioxide and monomethylamine at an elevated temperature and a higher pressure (JP-A 59-155364); and a reaction of ethylene carbonate with monoalkylamine (WO96/02516). These may be promising DMI preparation processes because they are a one-step reaction and the starting materials, i.e., N-alkylmonoethanolamine, ethylene glycol and ethylene carbonate, can be readily prepared from ethylene oxide with minimal byproducts. Based on our findings, however, a large amount of black solid is formed in these processes, which may block up a line during recycling all or a part of high boiling products into a reactor after collection of 1,3-dialkyl-2-imidazolidinone. These processes are, therefore, industrially impractical and thus have not been industrialized.

In addition, 1,3-dialkyl-2-imidazolidinones prepared according to these processes contain not a little amount of N-alkylformamide as an impurity, and thus are not suitable for use as a solvent.

Furthermore, commercially available DMI contains 1-methoxymethyl-3-methyl-2-imidazolidinone as an impurity, which may cause problems such as a reduced yield and a formation of byproducts when used as a reaction solvent or a polymerization solvent.

SUMMARY OF THE INVENTION

Thus, an object of this invention is to provide a process for manufacturing 1,3-dialkyl-2-imidazolidinones in a direct one-step reaction from industrially available alkylene carbonate, N-alkylmonoethanolamine or 1,2-diol, which can minimize forming solid materials and be readily conducted in an industrial large-scale production with a higher yield and less byproducts; as well as 1,3-dialkyl-2-imidazolidinone containing a minimal amount of 1-methoxymethyl-3-methyl-2-imidazolidinone according to the process.

We have intensely investigated a method for minimizing 1-alkoxyalkyl-3-alkyl-2-imidazolidinones as an impurity in 1,3-dialkyl-2-imidazolidinones and reducing formation of solid during the reaction, and have finally found that solid formation may be reduced, 1,3-dialkyl-2-imidazolidinones may be produced in a higher yield and 1-alkoxyalkyl-3-alkyl-2-imidazolidinones can be minimized by heating alkylene carbonate, N-alkylmonoethanolamine or ethylene glycol with monoalkylamine and carbon dioxide, alkylcarbamate alkylamine salt, and/or 1,3-dialkylurea at 50° C. or higher in a reactor whose area in contact with at least part of the reactants and/or products is made of (I) a metal comprising titanium or zirconium and/or an oxide thereof or (II) inorganic glasses.

Specifically, this invention provides;

(A) 1,3-dialkyl-2-imidazolidinones represented by general formula (1):

wherein $R^1$ is hydrogen or $C_1$–$C_6$ alkyl and $R^2$ is $C_1$–$C_6$ alkyl, containing 50 ppm by weight or less of 1-alkoxyalkyl-3-alkyl-2-imidazolidinones represented by general formula (2):

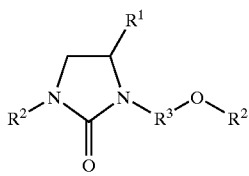
(2)

wherein $R^1$ and $R^2$ are as defined above; and $R^3$ is $C_1$–$C_6$ alkylene; or general formula (3):

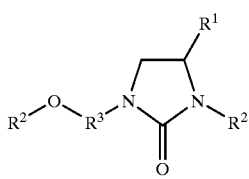
(3)

wherein $R^1$, $R^2$ and $R^3$ are as defined above;

(B) 1,3-dimethyl-2-imidazolidinone containing 50 ppm by weight or less of 1-methoxymethyl-3-methyl-2-imidazolidinone;

(C) 1,3-dialkyl-2-imidazolidinones described in (A) containing 0.5 wt % or less of N-alkylformamide represented by general formula (4):

$R^2$NHCHO (4)

wherein $R^2$ is as defined above;

(D) 1,3-dimethyl-2-imidazolidinone described in (B) containing 0.5 wt % or less of N-methylformamide;

(E) a process for manufacturing 1,3-dialkyl-2-imidazolidinones described in (A) or (C), comprising heating at 50° C. or higher alkylene carbonate represented by general formula (5):

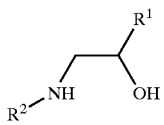
(5)

wherein $R^1$ is as defined above, with monoalkylamine represented by general formula (6):

$R^2$NH$_2$ (6)

wherein $R^2$ is as defined above; alkylcarbamate alkylamine salt represented by general formula (7):

$R^2$NHCOOH.$R^2$NH$_2$ (7)

wherein $R^2$ is as defined above; and/or 1,3-dialkylurea represented by general formula (8):

$R^2$NHCONHR$^2$ (8)

wherein $R^2$ is as defined above; in a reactor whose area in contact with at least part of the reactants and/or products is made of (I) a metal comprising titanium or zirconium and/or an oxide thereof or (II) inorganic glasses;

(F) a process described in (E) where the reaction is conducted in the presence of carbon dioxide;

(G) a process for manufacturing 1,3-dialkyl-2-imidazolidinones described in (A) or (C), comprising heating at 50° C. or higher N-alkylmonoethanolamine represented by general formula (9):

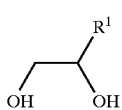
(9)

wherein $R^1$ and $R^2$ are as defined above; with
  i) monoalkylamine represented by general formula (6) and carbon dioxide,
  ii) alkylcarbamate alkylamine salt represented by general formula (7), and/or
  iii) 1,3-dialkylurea represented by general formula (8), in a reactor whose area in contact with at least part of the reactants and/or products is made of (I) a metal comprising titanium or zirconium and/or an oxide thereof or (II) inorganic glasses;

(H) a process for manufacturing 1,3-dialkyl-2-imidazolidinones described in (A) or (C), comprising heating at 50° C. or higher N-alkylmonoethanolamine represented by general formula (9) with alkylcarbamate alkylamine salt represented by general formula (7) and/or 1,3-dialkylurea represented by general formula (8) in the presence of carbon dioxide, in a reactor whose area in contact with at least part of the reactants and/or products is made of (I) a metal comprising titanium or zirconium and/or an oxide thereof or (II) inorganic glasses;

(I) a process for manufacturing 1,3-dialkyl-2-imidazolidinones described in (A) or (C), comprising heating at 50° C. or higher 1,2-diol represented by general formula (10):

(10)

wherein $R^1$ is as defined above; with
  i) monoalkylamine represented by general formula (6) and carbon dioxide,
  ii) alkylcarbamate alkylamine salt represented by general formula (7), and/or
  iii) 1,3-dialkylurea represented by general formula (8), in a reactor whose area in contact with at least part of the reactants and/or products is made of (I) a metal comprising titanium or zirconium and/or an oxide thereof or (II) inorganic glasses;

(J) a process for manufacturing 1,3-dialkyl-2-imidazolidinones described in (A) or (C), comprising heating at 50° C. or higher 1, 2-diol represented by general formula (10) with alkylcarbamate alkylamine salt represented by general formula (7) and/or 1,3-dialkylurea represented by general formula (8) in the presence of carbon dioxide, in a reactor whose area in contact with at least part of the reactants and/or products is made of (I) a metal comprising titanium or zirconium and/or an oxide thereof or (II) inorganic glasses;

(K) a process described in (E) for manufacturing 1,3-dimethyl-2-imidazolidinone described in (B) or (D), where alkylene carbonate is ethylene carbonate; monoalkylamine is monomethylamine; alkylcarbamate alkylamine salt is methylcarbamate methylamine salt; and 1,3-dialkylurea is 1,3-dimethylurea;

(L) a process described in (K) where the reaction is conducted in the presence of carbon dioxide;

(M) a process described in (G) for manufacturing 1,3-dimethyl-2-imidazolidinone described in (B) or (D), where N-alkylmonoethanolamine is 2-(methylamino) ethanol; monoalkylamine is monomethylamine; alkylcarbamate alkylamine salt is methylcarbamate methylamine salt; and 1,3-dialkylurea is 1,3-dimethylurea;

(N) a process described in (H) for manufacturing 1,3-dimethyl-2-imidazolidinone described in (B) or (D), wherein N-alkylmonoethanolamine is 2-(methylamino) ethanol; alkylcarbamate alkylamine salt is methylcarbamate methylamine salt; and 1,3-dialkylurea is 1,3-dimethylurea;

(O) a process described in (I) for manufacturing 1,3-dimethyl-2-imidazolidinone described in (B) or (D), wherein 1,2-diol is ethylene glycol; monoalkylamine is monomethylamine; alkylcarbamate alkylamine salt is methylcarbamate methylamine salt; and 1,3-dialkylurea is 1,3-dimethylurea;

(P) a process described in (J) for manufacturing 1,3-dimethyl-2-imidazolidinone described in (B) or (D), wherein 1,2-diol is ethylene glycol; alkylcarbamate alkylamine salt is methylcarbamate methylamine salt; and 1,3-dialkylurea is 1,3-dimethylurea;

(Q) a process described in any one of (E) to (P) where the reactor made of a metal comprising titanium or zirconium and/or an oxide thereof is a reactor which wholly consists of a metal comprising titanium or zirconium, or at least part of whose inside wall is coated with a metal comprising titanium or zirconium and/or an oxide thereof;

(R) a process described in (Q) where the reactor, at least part of the inside wall of which is coated with a metal comprising titanium or zirconium, is the reactor which is coated using a process selected from the group consisting of cladding processes such as rolling, explosive compaction, explosive rolling and casting rolling as well as baking process;

(S) a process described in (Q) where the reactor, at least part of the inside wall of which is coated with an oxide of a metal comprising titanium or zirconium, is the reactor which is coated using a method of forming an oxide film using an oxidizing agent;

(T) a process described in (Q) where the reactor, at least part of the inside wall of which is coated with an oxide of a metal comprising titanium or zirconium, is the reactor which is coated by means of thermal decomposition;

(U) a process described in any one of (E) to (P) where the metal comprising titanium or zirconium is selected from the group consisting of industrial pure titanium, corrosive resistant titanium-alloy and pure zirconium;

(V) a process described in any one of (E) to (P) where the reaction is conducted by heating at 100 to 300° C.; and (W) a process described in any one of (E) to (P) where 1,3-dialkyl-2-imidazolidinones represented by general formula (1) or water is used as a solvent.

According to the process of this invention, 1,3-dialkyl-2-imidazolidinones can be industrially effectively and readily produced. Furthermore, the process of this invention has a prominent characteristic that byproducts such as sodium chloride contaminated with organic compounds are not formed as in a conventional process.

DETAILED DESCRIPTION OF PREFERRED EMBODIMENTS

This invention will be described in detail.

This invention provides 1,3-dialkyl-2-imidazolidinones represented by general formula (1) containing 50 ppm or less of 1-alkoxyalkyl-3-alkyl-2-imidazolidinone represented by general formula (2) or (3).

In such formulas, $R^1$ is hydrogen or $C_1$–$C_6$ alkyl, $R^2$ is $C_1$–$C_6$ alkyl and $R^3$ is $C_1$–$C_6$ alkylene. Examples of 1-alkoxyalkyl-3-alkyl-2-imidazolidinone and 1-methoxymethyl-3-methyl-2-imidazolidinone, 1-methoxymethyl-3,4-dimethyl-2-imidazolidinone, 1-methoxymethyl-3,5-dimethyl-2-imidazolidinone, 1-(1-ethoxyethyl)-3-ethyl-2-imidazolidinone, 1-(2-ethoxyethyl)-3-ethyl-2-imidazolidinone, 1-(1-ethoxyethyl)-3-ethyl-4-methyl-2-imidazolidinone and 1-(2-ethoxyethyl)-3-ethyl-4-methyl-2-imidazolidinone.

Examples of 1,3-dialkyl-2-imidazolidinones are 1,3-dimethyl-2-imidazolidinone, 1,3,4-trimethyl-2-imidazolidinone, 1,3-dimethyl-4-ethyl-2-imidazolidinone, 1,3-dimethyl-4-isopropyl-2-imidazolidinone, 1,3-diethyl-2-imidazolidinone, 1,3-diethyl-4-methyl-2-imidazolidinone, 1,3-diisopropyl-2-imidazolidinone, 1,3-diisopropyl-4-methyl-2-imidazolidinone, 1,3-di-n-propyl-2-imidazolidinone, 1,3-di-n-propyl-4-methyl-2-imidazolidinone, 1,3-di-tert-butyl-2-imidazolidinone and 1,3-di-tert-butyl-4-methyl-2-imidazolidinone.

Preferably, 1-methoxymethyl-3-methyl-2-imidazolidinone can be used as 1-alkoxyalkyl-3-alkyl-2-imidazolidinone and 1,3-dimethyl-2-imidazolidinone can be used as 1,3-dialkyl-2-imidazolidinone. Thus, 1,3-dimethyl-2-imidazolidinone containing 50 ppm or less of 1-methoxymethyl-3-methyl-2-imidazolidinone is most preferable.

Furthermore, 1,3-dialkyl-2-imidazolidinone containing 0.5 wt % or less of N-alkylformamide represented by general formula (4) is preferable. Examples of N-alkylformamide are N-methylformamide, N-ethylformamide, N-isopropylformamide, N-n-propylformamide and N-tert-butylformamide; preferably N-methylformamide. Thus, 1,3-dimethyl-2-imidazolidinone containing 50 ppm or less of 1-methoxymethyl-3-methyl-2-imidazolidinone and 0.5 wt % or less of N-methylformamide is most preferable.

In this invention, 1,3-dialkyl-2-imidazolidinones can be prepared by heating at 50° C. or higher alkylene carbonate represented by general formula (5), with i) monoalkylamine represented by general formula (6), ii) alkylcarbamate alkylamine salt represented by general formula (7), and/or iii) 1,3-dialkylurea represented by general formula (8), in a reactor whose area in contact with at least part of the reactants and/or products is made of (I) a metal comprising titanium or zirconium and/or an oxide thereof or (II) inorganic glasses.

Alkylene carbonates represented by general formula (5) used as a starting material in the process of this invention include those in which $R^1$ is hydrogen or $C_1$–$C_6$ alkyl, such as ethylene carbonate and propylene carbonate, which may be readily prepared by heating carbon dioxide and alkylene oxide in the presence of a catalyst such as a quarternary ammonium salt. A commercially available alkylene carbonate may be used as it is in the process of this invention or it may be subject to a common purification process such as distillation before being used in the reaction.

Examples of monoalkylamines represented by general formula (6) as an another material in the process of this invention are those in which $R^2$ is $C_1-C_6$ alkyl, such as monomethylamine, monoethylamine, mono-n-propylamine, mono-isopropylamine, mono-n-butylamine, mono-sec-butylamine, mono-isobutylamine, mono-tert-butylamine and monocyclohexylamine; preferably monomethylamine and monoethylamine; more preferably monomethylamine.

The amount of monoalkylamine is generally, but not limited to, 0.1 to 200 moles, preferably 0.5 to 80 moles, more preferably 1.0 to 40 moles per one mole of alkylene carbonate.

Examples of alkylcarbamate alkylamine salt represented by general formual (7) as another material in the process of this invention are those in which R 2 is C1–C6 alkyl, such as methylcarbamate methylamine salt, ethylcarbamate ethylamine salt, n-propylcarbamate n-propylamine salt, isopropylcarbamate isopropylamine salt, n-butylcarbamate n-butylamine salt, sec-butylcarbamate secbutylamine salt, isobutylcarbamate isobutylamine salt, tert-butylcarbamate tert-butylamine salt and cyclohexylcarbamate cyclohexylamine salt, preferably methcarbamate methylamime salt and ethylcarbamate ethylamine salt; more preferably methylcarbamate methylamine salt.

Such alkylcarbamate alkylamine salt may be used as a solid or a solution such as an aqueous solution, or may be used as a combination of components generating the salt in the reaction system.

The amount of alkylcarbamate alkylamine salt is generally, but not limited to, 0.1 to 100 moles, preferably 0.5 to 40 moles, more preferably 1.0 to 20 moles per one mole of alkylene carbonate.

Examples of 1,3-dialkylurea represented by general formula (8) as an another material in the process of this invention are those in which $R^2$ is $C_1-C_6$ alkyl, such as 1,3-dimethylurea, 1,3-diethylurea, 1,3-di-n-propylurea, 1,3-di-isopropylurea, 1,3-di-n-butylurea, 1,3-di-sec-butylurea, 1,3-di-isobutylurea, 1,3-di-tert-butylurea and 1,3-dicyclohexylurea; preferably 1,3-dimethylurea and 1,3-diethylurea; more preferably 1,3-dimethylurea.

Commercially available 1,3-dialkylurea man be used as it is, or a combination of components generating 1,3-dialkylurea in the reaction system may be employed.

Carbon dioxide may be used as a gaseous, liquid or solid state in the process of this invention, or an inorganic carbonate such as ammonium carbonate, which provides carbon dioxide during the reaction, may be employed. The amount of carbon dioxide is generally, but not limited to, 0.1 to 1000 moles, preferably 1 to 1500 moles per one mole of alkylene carbonate.

Monoalkylamine, alkylcarbamate alkylamine salt and 1,3-dialkylurea may be used alone or concurrently or as a mixture.

Most preferably, ethylene carbonate can be used as an alkylene carbonate, monomethylamine can be used as a monoalkylamine, methylcarbamate methylamine salt can be used as an alkylcarbamate alkylamine salt and 1,3-dimethylurea can be used as a 1,3-dialkylurea, in the light of extensive applications of the product DMI therefrom as a solvent.

According to this invention, 1,3-dialkyl-2-imidazolidinones can be prepared by heating at 50° C. or higher N-alkylmonoethanolamine represented by general formula (9) with i) monoalkylamine represented by general formula (6) and carbon dioxide, ii) alkylcarbamate alkylamine salt represented by general formula (7) and/or iii) 1,3-dialkylurea represented by general formula (8), in a reactor whose area in contact with at least part of the reactants and/or products is made of (I) a metal comprising titanium or zirconium and/or an oxide thereof or (II) inorganic glasses.

Examples of N-alkylmonoethanolamine represented by general formula (9) as a material in the process of this invention are those in which $R^1$ is hydrogen or $C_1-C_6$ alkyl and $R^2$ is $C_1-C_6$ alkyl, such as 2-(methylamino)ethanol, 2-(ethylamino)ethanol, 2-(n-propylamino)ethanol, 2-(isopropylamino)ethanol, 2-(n-butylamino)ethanol, 2-(sec-butylamino)ethanol, 2-(isobutylamino)ethanol, 2-(tert-butylamino)ethanol, 2-(n-amylamino)ethanol, 2-(isoamylamino)ethanol, 2-(2-methylbutylamino)ethanol, 2-(1-methylbutylamino)ethanol, 2-(n-hexylamino)ethanol, n-cyclohexylethanolamine, 1-methylamino-2-propanol, 1-ethylamino-2-propanol, 1-(n-propylamino)-2-propanol, 1-(isopropylamino)-2-propanol, 1-(n-butylamino)-2-propanol, 1-(n-amylamino)-2-propanol, 1-methylamino-2-butanol, 1-methylamino-2-pentanol, 1-methylamino-2-hexanol and 1-methylamino-2-octanol; preferably 2-(methylamino)ethanol, 2-(ethylamino)ethanol, 2-(isopropylamino)ethanol and 1-methylamino-2-propanol; more preferably 2-(methylamino)ethanol.

Commercially available N-alkylmonoethanolamine may be used as it is, or may be subject to a common purification process such as distillation before being used in the reaction.

Monoalkylamine represented by general formula (6) may be the same as described above. The amount thereof is generally, but not limited to, 0.1 to 100 moles, preferably 0.3 to 40 moles, more preferably 0.5 to 20 moles per one mole of N-alkylmonoethanolamine.

The amount of carbon dioxide is generally, but not limited to, 0.1 to 200 moles, preferably 1 to 100 moles per one mole of N-alkylmonoethanolamine.

Alkylcarbamate alkylamine salt represented by general formula (7) may be the same as described above. The amount thereof is generally, but not limited to, 0.1 to 50 moles, preferably 0.3 to 20 moles, more preferably 0.5 to 10 moles per one mole of N-alkylmonoethanolamine.

Then, 1,3-dialkylurea represented by general formula (8) may be the same as described above. The amount thereof is generally, but not limited to, 0.1 to 50 moles, preferably 0.3 to 20 moles, more preferably 0.5 to 10 moles per one mole of N-alkylmonoethanolamine.

(a)Monoalkylamine and carbon dioxide, (b)alkylcarbamate alkylamine salt and (c)1,3-dialkylurea may be used alone or concurrently or as a mixture.

Most preferably, 2-(methylamino)ethanol can be used as a N-alkylmonoethanolamine, monomethylamine can be used as a monoalkylamine, methylcarbamate methylamine salt can be used as an alkylcarbamate alkylamine salt and 1,3-dimethylurea can be used as a 1,3-dialkylurea, in the light of extensive applications of the product DMI therefrom as a solvent.

According to this invention, 1,3-dialkyl-2-imidazolidinones can be prepared by heating at 50° C. or higher N-alkylmonoethanolamine represented by general formula (9) with alkylcarbamate alkylamine salt represented by general formula (7) and/or 1,3-dialkylurea represented by general formula (8) in the presence of carbon dioxide, in a reactor whose area in contact with at least part of the reactants and/or products is made of (I) a metal comprising titanium or zirconium and/or an oxide thereof or (II) inorganic glass.

N-alkylmonoethanolamine represented by general formula (9) used as a starting material in this invention process may be the same as described above.

Alkylcarbamate alkylamine salt represented by general formula (7) may be the same as described above. The amount thereof is generally, but not limited to, 0.1 to 50 moles, preferably 0.3 to 20 moles, more preferably 0.5 to 10 moles per one mole of N-alkylmonoethanolamine.

1,3-Dialkylurea represented by general formula (8) may be the same as described above. The amount thereof is generally, but not limited to, 0.1 to 50 moles, preferably 0.3 to 20 moles, more preferably 0.5 to 10 moles per one mole of N-alkylmonoethanolamine.

This reaction is preferably conducted in an atmosphere of carbon dioxide. The amount of carbon dioxide is generally, but not limited to, 0.1 to 1000 moles, preferably 1 to 500 moles per one mole of N-alkylmonoethanolamine.

Alkylcarbamate alkylamine salt and 1,3-dialkylurea may be used alone or concurrently or as a mixture.

Most preferably, 2-(methylamino)ethanol can be used as an N-alkylmonoethanolamine, methylcarbamate methylamine salt can be used as an alkylcarbamate alkylamine salt and 1,3-dimethylurea can be used as a 1,3-dialkylurea, in the light of extensive applications of the product DMI therefrom as a solvent.

According to this invention, 1,3-dialkyl-2-imidazolidinones can be also prepared by heating at 50° C. or higher 1,2-diol represented by general formula (10) with i) monoalkylamine represented by general formula (6) and carbon dioxide, ii) alkylcarbamate alkylamine salt represented by general formula (7) and/or iii) 1,3-dialkylurea represented by general formula (8), in a reactor whose area in contact with at least part of the reactants and/or products is made of (I) a metal comprising titanium or zirconium and/or an oxide thereof or (II) inorganic glass.

Examples of 1,2-diol represented by general formula (10) as a material in this invention process are those in which $R^1$ is hydrogen or $C_1$-$C_6$ alkyl, such as ethylene glycol, 1,2-propanediol, 1,2-butanediol, 1,2-pentanediol, 1,2-hexanediol and 1,2-octanediol; preferably ethylene glycol and 1,2-propanediol; more preferably ethylene glycol.

Commercially available 1,2-diol may be used as it is, or may be subject to a common purification process such as distillation before being used in the reaction.

Monoalkylamine represented by general formula (6) may be the same as described above. The amount thereof is generally, but not limited to, 0.1 to 200 moles, preferably 0.5 to 80 moles, more preferably 1.0 to 40 moles per one mole of 1,2-diol.

The amount of carbon dioxide is generally, but not limited to, 0.1 to 200 moles, preferably 1 to 100 moles per one mole of 1,2-diol.

Alkylcarbamate alkylamine salt represented by general formula (7) may be the same as described above. The amount thereof is generally, but not limited to, 0.1 to 100 moles, preferably 0.5 to 40 moles, more preferably 1.0 to 20 moles per one mole of 1,2-diol.

Then, 1,3-dialkylurea represented by general formula (8) may be the same as described above. The amount thereof is generally, but not limited to, 0.1 to 100 moles, preferably 0.5 to 40 moles, more preferably 1.0 to 20 moles per one mole of 1,2-diol.

a)Monoalkylamine and carbon dioxide, b)alkylcarbamate alkylamine salt and c)1,3-dialkylurea may be used alone or concurrently or as a mixture.

Most preferably, ethylene glycol can be used as a 1,2-diol, monomethylamine can be used as a monoalkylamine, methylcarbamate methylamine salt can be used as an alkylcarbamate alkylamine salt and 1,3-dimethylurea can be used as a 1,3-dialkylurea, in the light of extensive applications of the product DMI therefrom as a solvent.

According to this invention, 1,3-dialkyl-2-imidazolidinones can be also prepared by heating at 50° C. or higher 1,2-diol represented by general formula (10) with alkylcarbamate alkylamine salt represented by general formula (7) and/or 1,3-dialkylurea represented by general formula (8) in the presence of carbon dioxide, in a reactor whose area in contact with at least part of the reactants and/or products is made of (I) a metal comprising titanium or zirconium and/or an oxide thereof or (II) inorganic glass.

The 1,2-diol represented by general formula (10) may be the same as described above.

Alkylcarbamate alkylamine salt represented by general formula (7) may be the same as described above. The amount thereof is generally, but not limited to, 0.1 to 100 moles, preferably 0.5 to 40 moles, more preferably 1.0 to 20 moles per one mole of 1,2-diol.

The 1,3-dialkylurea represented by general formula (8) may be the same as described above. The amount thereof is generally, but not limited to, 0.1 to 100 moles, preferably 0.5 to 40 moles, more preferably 1.0 to 20 moles per one mole of 1,2-diol.

The reaction is conducted in an atmosphere of carbon dioxide. The atmosphere of the reaction is preferably of carbon dioxide. The amount of carbon dioxide is generally, but not limited to, 0.1 to 1000 moles, preferably 1 to 500 moles per one mole of 1,2-diol.

Alkylcarbamate alkylamine salt and 1,3-dialkylurea may be used alone or concurrently or as a mixture.

Most preferably, ethylene glycol can be used as a 1,2-diol, methylcarbamate methylamine salt can be used as an alkylcarbamate alkylamine salt and 1,3-dimethylurea can be used as a 1,3-dialkylurea, in the light of extensive applications of the product DMI therefrom as a solvent.

A reactor used in the process of this invention is one whose area in contact with at least part of the reactants and/or products is made of (I) a metal comprising titanium or zirconium and/or an oxide thereof or (II) inorganic glass. It may be, for example, wholly made of a metal comprising titanium or zirconium. Alternatively, at least part of the inside wall of the reactor is coated with a metal comprising titanium or zirconium or an oxide thereof, or the inside wall may be coated with inorganic glass. Examples of a metal comprising titanium or zirconium are industrial pure titaniums of JIS Types 1 to 4; corrosive resistant titanium alloys such as Ti—0.15Pd, Ti—5Ta and Ti—0.3Mo—0.8Ni; α-type titanium alloys such as Ti—2.5Sn, Ti—5Al—2.5Sn, Ti—5Al—2.5Sn(ELI), Ti—2.5Cu, Ti—20— 1N—5Fe, Ti—5Ni—0.5Ru, Ti—0.5Pd—3Co and Ti—5.5Al—3.5Sn—3Zr—1Nb—0.3Mo—0.3Si; near α-type titanium alloys such as Ti—8Al—1Mo—1V, Ti—2.25Al—11Sn—5Zr—1Mo—0.2Si, Ti—6Al—2Sn—4Zr—2Mo, Ti—5Al—5Sn—2Zr—2Mo—0.25Sn, Ti—6Al—2Nb—1Ta—0.8Mo, Ti—6Al—5Zr—0.5Mo—0.2Si and Ti—4.5Al—3V—2Fe—2Mo; α+β type titanium alloys such as Ti—5Al—2Cr—1Fe, Ti—5Al—5Sn—5Zr—2Cr—1Fe, Ti—4Al—4Mn, Ti—3Al—2.5V, Ti—6Al—4V, Ti—6Al—4V(ELI), Ti—6Al—6V—2Sn, Ti—6Al—2Sn—4Zr—6Mo, Ti—7Al—4Mo, Ti—5Al—2Zr—4Mo—4Cr, Ti—6Al—1.7Fe—0.1Si, Ti—6.4Al—1.2Fe, Ti—15Zr—4Nb—2Ta—2Pd, Ti—6Al—7Nb and Ti—8Mn; β type titanium alloys such as Ti—13V—11Cr—3Al, Ti—15Mo—5Zr, Ti—15Mo—0.2Pd, Ti—15V—3Cr—3Sn—3Al, Ti—20V—4Al—1Sn, Ti—22V—4Al and Ti—16V—

4Sn—3Al—3Nb; near β type titanium alloys such as Ti—10V—2Fe—3Al and Ti—9.5V—2.5Mo—3Al; pure zirconium; and zirconium alloys such as zircaloy-2, zircaloy-4, Zr—2.5Nb and Ozenite; preferably titanium-containing metals and pure zirconium; more preferably industrial pure titanium, corrosion resisting titanium alloys and pure zirconium. The content of titanium or zirconium in the metal comprising titanium or zirconium or the oxide thereof is generally at least 30 mol %, preferably at least 50 mol %, more preferably at least 60 mol % to the whole metal elements. The inside wall may be coated with the metal by a process selected from cladding, baking, flame spray coating, vapor deposition, decomposition and any combination thereof. Among them, cladding processes such as rolling, explosive compaction, explosive rolling and casting rolling as well as baking process may be preferably employed. The inside wall may be coated with an oxide film by the process of thermal decomposition, baking, flame coating, forming an oxide film on the metal surface of the inside wall of the reactor using an oxidizing agent or a combination thereof. Among others, preferable processes are, for example, $PdO/TiO_2$ coating by thermal decomposition of $PdCl_2$ and $TiCl_3$, or forming an oxide film using an oxidizing agent such as oxygen-containing gases including oxygen and air; peroxides including hydrogen peroxide and peracetic acid; and nitric-acid agents including nitric acid and a mixture of nitric acid and hydrofluoric acid. The oxide film may be formed on the inside wall of the reactor before conducting the reaction. Alternatively, the oxide film may be formed by incorporating an oxidizing agent in the reaction system, while heating alkylene carbonate, N-alkylmonoethanolamine or 1,2-diols with monoalkylamine and carbon dioxide, alkylcarbamate alkylamine salt and/or 1,3-dialkylurea. These coating methods may be further combined. For example, the inside wall may be coated with a metal comprising titanium or zirconium by the process of cladding or baking or a combination thereof, followed by forming an oxide film over the metal surface using an oxidizing agent.

A reactor comprising inorganic glasses may be a reactor wholly made of inorganic glasses, a metal reactor in which an inorganic glass cup is placed, or a metal reactor lined with inorganic glass; preferably a metal reactor lined with inorganic glass.

Inorganic glasses in the present invention are a glassy state of inorganic material such as elemental glasses, hydrogen-bonding glasses, oxide glasses, fluoride glasses, chloride glasses, sulfide glasses, carbonate glasses, nitride glasses and sulfate glasses; preferably oxide glasses including silicate glass, phosphate glass and borate glass; particularly, silicate glasses including silica glasses such as quartz glass, silicate alkali glasses such as water glass, soda-lime glasses such as sheet glass and crown glass, potash lime glasses such as Bohemian glass and crystal glass, lead glasses such as flint glass, barium glasses such as barium flint glass and borosilicate glasses such as electrical glass; more preferably, soda-lime glasses; most preferably, soda-lime glasses containing aluminum, magnesium or calcium ion as a modifying ion.

Preferably, 50 to 100%, more preferably 80 to 100% of the area in contact with reactants and/or products is made of (I) a metal comprising titanium or zirconium or (II) inorganic glass. More preferably, the whole reactor including a gas phase region is made of (I) a metal comprising titanium or zirconium and/or an oxide thereof or (II) inorganic glasses, although a reactor comprising (I) rather than (II) is preferable for a reaction conducted at a pressure of 5 MPa or higher.

A style of the process of this invention is not particularly limited, and may be any style in which materials used are effectively mixed and contacted with each other, including a batch, semi-batch or continuous flow type. For example, all materials may be placed in a reactor together; at least one material may be continuously or intermittently added to the other materials; or all materials are continuously or intermittently fed into a reactor.

In the process of this invention, reactants are heated at 50° C. or higher, preferably at 50 to 400° C., more preferably 100 to 300° C.

A reaction time and a pressure may vary depending on the amount of materials, a reaction temperature and other factors, but a reaction time is generally up to 200 hours, preferably 0.01 to 100 hours, more preferably 0.1 to 50 hours. The reaction is generally conducted under a pressure, preferably at 0.1 to 50 MPa, more preferably 0.2 to 20 MPa.

A gas used for replacing or pressurizing a reaction system may be, but not limited to, an inert gas such as nitrogen and argon or preferably carbon dioxide. Carbon dioxide may be used as a gaseous, liquid or solid state, or may be introduced as an inorganic carbonate such as ammonium carbonate which generates carbon dioxide during the reaction.

In the process of this invention, a reaction is generally conducted without solvent, but may be conducted in the presence of a solvent. Any solvent which does not adversely affect the reaction may be used. Solvents which may be used include water; aliphatic and alicyclic hydrocarbons such as pentane, hexane, heptane, octane, cyclohexane and methylcyclohexane; aromatic hydrocarbons such as benzene, toluene and xylenes; aliphatic and aromatic halogenated compounds such as dichloromethane, chloroform, fluorobenzene, chlorobenzene and dichlorobenzene; ethers such as diethyl ether, methyl tert-butyl ether, dibutyl ether, diphenyl ether, tetrahydrofuran, dioxane and ethylene glycol diethyl ether; ketones such as acetone, diethyl ketone; methyl isobutyl ketone and acetophenone; nitrites such as acetonitrile and propionitrile; nitro compounds such as nitromethane, nitrobenzene and nitrotoluene; esters such as ethyl acetate and ethyl propionate; carbonates such as dimethyl carbonate; noncyclic and cyclic amides such as N,N-dimethylformamide, N,N-diethylformamide, N,N-dimethylacetamide and N-methyl-2-pyrrolidone; cyclic urea compounds such as 1,3-dialkyl-2-imidazolidinones including DMI (the product of the process of this invention); and supercritical fluids such as supercritical carbon dioxide. Further, these solvents may be used alone or in combination of two kinds or more at the same time, and if such solvents be used, the reaction may be carried out in a multi-layer system of two or more layer solvents. Among these solvents, 1,3-dialkyl-2-imidazolidinone, which is the product of the process of this invention, and water are preferable.

Such a solvent may be used at an amount sufficient to dissolve at least one of the starting materials, generally up to 100 parts by weight, preferably up to 50 parts by weight per one part of alkylene carbonates, N-alkyl monoethanolamines, or 1,2-diols, a starting material.

In the process of this invention, a catalyst and/or an additive may be added for improving an yield and a reaction rate.

In the process of this invention, at the end of the reaction, a reaction mixture may be worked up as usual, for example, via distillation, to give 1,3-dialkyl-2-imidazolidinones. The 1,3-dialkyl-2-imidazolidinone thus obtained includes 50 ppm or less of 1-alkoxyalkyl-3-alkyl-2-imidazolidinone which is a common impurity in a conventional process, and 0.5 wt % or less of N-alkylformamide.

This invention will be, but not limited to, specifically described with reference to Examples.

EXAMPLE 1

In a 400 mL (inner volume) autoclave whose lid, stirring rod and stirring blades were made of JIS type 2 of industrial pure titanium, and an inner surface whose body was lined with JIS type 2 of industrial pure. titanium, were placed 44.0 g of ethylene carbonate (0.5 mol) and 18.0 g of ion exchange water (1.0 mol). After the gas phase was replaced with nitrogen, 93.2 g of monomethylamine (3.0 mol) was charged. Then, while externally heating the autoclave, these materials were reacted under stirring at an internal temperature of 210° C. for 24 hours.

The autoclave was cooled and the reaction liquid was removed. The reaction liquid was light yellow, in which solid material formation was not observed.

Gas chromatography for the reaction liquid indicated that a conversion rate of ethylene carbonate was 99%, an yield of the product DMI to the charged ethylene carbonate (hereinafter, referred to as a "DMI yield") was 42%, and a total yield of byproducts, 1,4-dimethylpiperadine, ethylene glycol and 2-(methylamino)ethanol was 38%.

The reaction liquid was distilled to give 22.8 g of 1,3-dimethyl-2-imidazolidinone whose purity was 99%.

In the DMI, 1-methoxymethyl-3-methyl-2-imidazolidinone was not included and 0.3 wt % of N-methyl formamide was included.

Comparative Example 1

A reaction was conducted as described in Example 1, except that a 400 mL (inner volume) autoclave made of SUS-316L was used.

After cooling the autoclave, the reaction liquid was removed. Since black solids floating in the liquid were observed, the liquid was filtered to give a brown filtrate. The dry weight of the black solids was 3.21 g.

Gas chromatography for the filtrate indicated that a conversion rate of ethylene carbonate was 99%, a DMI yield was 38%, and a total yield of byproducts, 1,4-dimethylpiperadine, ethylene glycol and 2-(methylamino) ethanol was 44%.

The reaction liquid was distilled in vacuo to give 20.1 g of 1,3-dimethyl-2-imidazolidinone whose purity was 99%. In DMI, 0.8 wt % of N-methyl formamide was included.

EXAMPLE 2

In the autoclave described in Example were placed the materials described in Example 1. Then, 44.0 g of carbon dioxide was charged in the reaction system. They were reacted as described in Example 1. After the reaction, the reaction liquid was light yellow, in which solid material formation was not observed.

Gas chromatography for the reaction liquid as described in Example 1 indicated that a conversion rate of ethylene carbonate was 99%, a DMI yield was 68%, and a total yield of byproducts, 1,4-dimethylpiperadine, ethylene glycol and 2-(methylamino)ethanol was 15%.

Comparative Example 2

Using the autoclave described in Comparative Example 1, the materials were placed and reacted as described in Example 2. After the reaction, there were observed floating black solid materials. The liquid was filtered as described in Comparative Example 1 to give a brown filtrate. The dry weight of the black solids was 4.12 g.

Gas chromatography for the filtrate as described in Comparative Example 1 indicated that a conversion rate of ethylene carbonate was 99%, a DMI yield was 66%, and a total yield of byproducts, 1,4-dimethylpiperadine, ethylene glycol and 2-(methylamino)ethanol was 18%.

EXAMPLE 3

In the autoclave described in Example 1 were placed 44.0 g of ethylene carbonate (0.5 mol), 132.2 g of 1,3-dimethylurea (1.5 mol) and 36.0 g of ion exchange water (2.0 mol). After the gas phase was replaced with nitrogen, 31.1 g of monomethylamine (1.0 mol) was charged. Then, while externally heating the autoclave, these materials were reacted under stirring at an internal temperature of 240° C. for 18 hours. After the reaction, the reaction liquid was light yellow, in which solid material formation was not observed.

Gas chromatography for the reaction liquid as described in Example 1 indicated that a conversion rate of ethylene carbonate was 99%, a DMI yield was 76%, and a total yield of byproducts, 1,4-dimethylpiperadine, ethylene glycol and 2-(methylamino)ethanol was 13%.

Comparative Example 3

Using the autoclave described in Comparative Example 1, the materials were placed and reacted as described in Example 3. After the reaction, there were observed floating black solid materials. The liquid was filtered as described in Comparative Example 1 to give a brown filtrate. The dry weight of the black solids was 4.21 g.

Gas chromatography for the filtrate as described in Comparative Example 1 indicated that a conversion rate of ethylene carbonate was 99%, a DMI yield was 73%, and a total yield of byproducts, 1,4-dimethylpiperadine, ethylene glycol and 2-(methylamino)ethanol was 16%.

EXAMPLE 4

In a 80 mL (inner volume) autoclave made of SUS-316L, which is equipped with a cylindrical vessel, a stirring rod and stirring blades, which are made of Ti—0.15Pd, were placed 7.0 g of ethylene carbonate (0.08 mol), 34.0 g of methylcarbamate methylamine salt (0.32 mol) and 4.3 g of ion exchange water (0.24 mol). After the gas phase was replaced with nitrogen, 5.0 g of monomethylamine (0.16 mol) was charged. Then, while externally heating the autoclave, these materials were reacted under stirring at an internal temperature of 220° C. for 24 hours. After the reaction, the reaction liquid was light yellow, in which solid material formation was not observed.

Gas chromatography for the reaction liquid as described in Example 1 indicated that a conversion rate of ethylene carbonate was 99%, a DMI yield was 77%, and a total yield of byproducts, 1,4-dimethylpiperadine, ethylene glycol and 2-(methylamino)ethanol was 13%.

Comparative Example 4

Using a 80 mL (inner volume) autoclave made of SUS-316L, the materials were placed and reacted as described in Example 4. After the reaction, there were observed floating black solid mate rials. The liquid was filtered as described in Comparative Example 1 to give a brown filtrate. The dry weight of the black solids was 0.70 g.

Gas chromatography for the filtrate as described in Comparative Example 1 indicated that a conversion rate of ethylene carbonate was 99%, a DMI yield was 73%, and a total yield of byproducts, 1,4-dimethylpiperadine, ethylene glycol and 2-(methylamino) ethanol was 17%.

EXAMPLE 5

In a 80 mL (inner volume) autoclave made of SUS-316L, which is equipped with a cylindrical vessel, a stirring rod and stirring blades, which are made of Ti—6Al—4V, were placed 8.2 g of propylene carbonate (0.08 mol), 25.5 g of methylcarbamate methylamine salt (0.24 mol) and 5.8 g of ion exchange water (0.32 mol). After the gas phase was replaced with nitrogen, 5.0 g of monomethylamine (0.16 mol) was charged. Then, while externally heating the autoclave, these materials were reacted under stirring at an internal temperature of 240° C., for 15 hours. After the reaction, the reaction liquid was light yellow, in which solid material formation was not observed.

Gas chromatography for the reaction liquid as described in Example 1 indicated that a conversion rate of propylene carbonate was 99%, an yield of the product 1,3,4-trimethyl-2-imidazolidinone to propylene carbonate charged was 52%, and a total yield of byproducts, 1,2,4-trimethylpiperadine, propylene glycol and 1-methylamino-2-propanol was 37%.

Comparative Example 5

Using a 80 mL (inner volume) autoclave made of SUS-316L, the materials were placed and reacted as described in Example 5. After the reaction, there were observed floating black solid materials. The liquid was filtered as described in Comparative Example 1 to give a brown filtrate. The dry weight of the black solids was 0.60 g.

Gas chromatography for the filtrate as described in Comparative Example 1 indicated that a conversion rate of propylene carbonate was 99%, an yield of the product 1,3,4-trimethyl-2-imidazolidinone to propylene carbonate charged was 48%, and a total yield of byproducts, 1,2,4-trimethylpiperadine, propylene glycol and 1-methylamino-2-propanol was 42%.

EXAMPLE 6

In the autoclave described in Example 1 were placed 75.1 g of 2-(methylamino)ethanol (1.0 mol) and then 129.5 g of 53.3 wt % methylcarbamate methylamine salt solution, and the gas phase was replaced with nitrogen. Then, while externally heating the autoclave, these materials were reacted under stirring at an internal temperature of 250° C. for 5 hours. After the reaction, the reaction liquid was light yellow, in which solid material formation was not observed.

Gas chromatography for the reaction liquid as described in Example 1 indicated that a conversion rate of 2-(methylamino)ethanol was 99%, an yield of DMI to 2-(methylamino)ethanol charged (hereinafter, referred to as a "DMI" yield) was 75%, and an yield of a byproduct 1,4-dimethylpiperadine was 17%.

Comparative Example 6

Using the autoclave described in Comparative Example 1, the materials were placed and reacted as described in Example 6. After the reaction, there were observed floating black solid materials. The liquid was filtered to give a brown filtrate. The dry weight of the black solids was 3.15 g.

Gas chromatography for the filtrate indicated that a conversion rate of 2-(methylamino)ethanol was 99%, a DMI yield was 69%, and an yield of a byproduct 1,4-dimethylpiperadine was 25%.

EXAMPLE 7

In a 25 mL glass (Pyrex™) ampule were placed 0.526 g of 2-(methylamino)ethanol (7.0 mmol), 7.43 g of methylcarbamate methylamine salt (70 mmol) and 6.53 g of ion exchange water (360 mmol). After the gas phase was replaced with nitrogen, the ampule was closed. The ampule was placed in a 400 mL (inner volume) autoclave made of SUS-316L, and then 200 mL of water was placed in the autoclave, which was then pressurized with $N_2$ to 2 MPa. Then, while externally heating the autoclave, these materials were reacted at an internal temperature of 200° C. for 18 hours. After the reaction, the reaction liquid was colorless, in which solid material formation was not observed.

Gas chromatography for the reaction liquid as described in Example 1 indicated that a conversion rate of 2-(methylamino)ethanol was 99%, an yield of DMI was 94%, and an yield of a byproduct 1,4-dimethylpiperadine was 4%.

Comparative Example 7

In a 50 mL (inner volume) autoclave made of SUS-316L were placed 1.05 g of 2-(methylamino)ethanol (14 mmol), 14.86 g of methylcarbamate methylamine salt (140 mmol) and 13.0 g of ion exchange water (720 mmol), and the gas phase was replaced with nitrogen. Then, while externally heating the autoclave, these materials were reacted under stirring at an internal temperature of 200° C. for 18 hours. After the reaction, there were observed floating black solid materials. The liquid was filtered as described in Comparative Example 1 to give a brown filtrate. The dry weight of the black solids was 0.33 g.

Gas chromatography for the filtrate indicated that a conversion rate of 2-(methylamino)ethanol was 99%, a DMI yield was 79%, and an yield of a byproduct 1,4-dimethylpiperadine was 15%.

EXAMPLE 8

In the autoclave described in Example 1 was placed 30.0 g of 2-(methylamino)ethanol (0.4 mol), and the gas phase was replaced with nitrogen. In the autoclave were then charged 74.6 g of monomethylamine (2.4 mol) and 52.8 g of carbon dioxide (1.2 mol). Then, while externally heating the autoclave, these materials were reacted under stirring at an internal temperature of 230° C. for 6 hours. After the reaction, the reaction liquid was light yellow, in which solid material formation was not observed.

Gas chromatography for the reaction liquid as described in Example 1 indicated that a conversion rate of 2-(methylamino)ethanol was 96%, a DMI yield was 72%, and an yield of a byproduct 1,4-dimethylpiperadine was 17%.

The reaction liquid was distilled in vacuo to give 31.0 g of 1,3-dimethyl-2-imidazolidinone whose purity was 99%.

Comparative Example 8

Using the autoclave described in Comparative Example 1, the materials were placed and reacted as described in Example 8. After the reaction, there were observed floating black solid materials. The liquid was filtered to give a brown filtrate. The dry weight of the black solids was 2.33 g.

Gas chromatography for the filtrate indicated that a conversion rate of 2-(methylamino)ethanol was 95%, a DMI yield was 63%, and an yield of a byproduct 1,4-dimethylpiperadine was 25%.

The filtrate was distilled in vacuo to give 26.9 g of 1,3-dimethyl-2-imidazolidinone whose purity was 99%.

EXAMPLE 9

In the autoclave described in Example 1 were placed 15.0 g of 2-(methylamino)ethanol (0.2 mol), 176.2 g of 1,3-dimethylurea (2.0 mol) and 72.0 g of ion exchange water (4.0 mol), and then the gas phase was replaced with nitrogen. Then, while externally heating the autoclave, these materials were reacted under stirring at an internal temperature of 230° C. for 7 hours. After the reaction, the reaction liquid was light yellow, in which solid material formation was not observed.

Gas chromatography for the reaction liquid as described in Example 1 indicated that a conversion rate of 2-(methylamino)ethanol was 99%, a DMI yield was 82%, and an yield of a byproduct 1,4-dimethylpiperadine was 8%.

Comparative Example 9

Using the autoclave described in Comparative Example 1, the materials were placed and reacted as described in Example 9. After the reaction, there were observed floating black solid materials. The liquid was filtered as described in Comparative Example 1 to give a brown filtrate. The dry weight of the black solids was 2.53 g.

Gas chromatography for the filtrate as described in Comparative Example 1 indicated that a conversion rate of 2-(methylamino)ethanol was 99%, a DMI yield was 74%, and an yield of a byproduct 1,4-dimethylpiperadine was 15%.

EXAMPLE 10

In a 80 mL (inner volume) autoclave made of SUS-316L which is equipped with a cylindrical vessel, a stirring rod and stirring blades, which are made of Ti—0.15Pd, were placed 6.0 g of 2-(methylamino)ethanol (0.08 mol), 34.0 g of methylcarbamate methylamine salt (0.32 mol) and 2.9 g of ion exchange water (0.16 mol), and the gas phase was replaced with nitrogen. Then, while externally heating the autoclave, these materials were reacted under stirring at an internal temperature of 220° C. for 8 hours. After the reaction, the reaction liquid was light yellow, in which solid material formation was not observed.

Gas chromatography for the reaction liquid as described in Example 1 indicated that a conversion rate of 2-(methylamino)ethanol was 99%, a DMI yield was 78%, and an yield of a byproduct 1,4-dimethylpiperadine was 14%.

Comparative Example 10

Using a 80 mL (inner volume) autoclave made of SUS-316L, the materials were placed and reacted as described in Example 10. After the reaction, there were observed floating black solid materials. The liquid was filtered as described in Comparative Example 1 to give a brown filtrate. The dry weight of the black solids was 0.37 g.

Gas chromatography for the filtrate as described in Comparative Example 1 indicated that a conversion rate of 2-(methylamino)ethanol was 99%, a DMI yield was 68%, and an yield of a byproduct 1,4-dimethylpiperadine was 22%.

EXAMPLE 11

In a 80 mL (inner volume) autoclave made of SUS-316L which is equipped with a cylindrical vessel, a stirring rod and stirring blades, which are made of Ti—6Al—4V, were placed 7.9 g of 1-ethylamino-2-propanol (0.08 mol), 32.2 g of ethylcarbamate ethylamine salt (0.24 mol) and 1.4 g of ion exchange water (0.08 mol), and then the gas phase was replaced with nitrogen. Then, while externally heating the autoclave, these materials were reacted under stirring at an internal temperature of 220° C. for 6 hours. After the reaction, the reaction liquid was light yellow, in which solid material formation was not observed.

Gas chromatography for the reaction liquid as described in Example 1 indicated that a conversion rate of 1-ethylamino-2-propanol was 85%, an yield of the product 1,3-diethyl-4-methyl-2-imidazolidinone to 1-ethylamino-2-propanol charged was 61%, and an yield of a byproduct 1,4-diethyl-2-methylpiperadine was 14%.

Comparative Example 11

Using a 80 mL (inner volume) autoclave made of SUS-316L, the materials were placed and reacted as described in Example 11. After the reaction, there were observed floating black solid materials. The liquid was filtered as described in Comparative Example 1 to give a brown filtrate. The dry weight of the black solids was 0.34 g.

Gas chromatography for the filtrate as described in Comparative Example 1 indicated that a conversion rate of 1-ethylamino-2-propanol was 82%, an yield of the product 1,3-diethyl-4-methyl-2-imidazolidinone to 1-ethylamino-2-propanol charged was 52%, and an yield of a byproduct 1,4-diethyl-2-methylpiperadine was 21%.

EXAMPLE 12

In the autoclave described in Example 1 were placed 30.0 g of 2-(methylamino)ethanol (0.4 mol), 127.3 g of methylcarbamate methylamine salt (1.2 mol) and 43.3 g of ion exchange water (2.4 mol), and the gas phase was replaced with nitrogen. Then, while externally heating the autoclave, these materials were reacted under stirring at an internal temperature of 200° C. for 6 hours. After the reaction, the reaction liquid was light yellow, in which solid material formation was not observed.

Gas chromatography for the reaction liquid as described in Example 1 indicated that a conversion rate of 2-(methylamino)ethanol was 35%, a DMI yield was 25%, and an yield of a byproduct 1,4-dimethylpiperadine was 5%.

The reaction liquid was distilled in vacuo to give 9.8 g of 1,3-dimethyl-2-imidazolidinone whose purity was 99%.

Comparative Example 12

Using the autoclave described in Comparative Example 1, the materials were placed and reacted as described in Example 12. After the reaction, there were observed floating black solid materials. The liquid was filtered as described in Comparative Example 1 to give a brown filtrate. The dry weight of the black solids was 1.69 g.

Gas chromatography for the filtrate indicated that a conversion rate of 2-(methylamino)ethanol was 38%, a DMI yield was 21%, and an yield of a byproduct 1,4-dimethylpiperadine was 8%.

The reaction liquid was distilled in vacuo to give 9.1 g of 1,3-dimethyl-2-imidazolidinone whose purity was 99%.

EXAMPLE 13

Using the autoclave described in Example 1, the materials were placed and reacted as described in Example 12, and then 52.8 g of carbon dioxide (1.2 mol) was charged in the reaction system. Then, while externally heating the autoclave, these materials were reacted under stirring at an internal temperature of 200° C. for 6 hours. After the reaction, the reaction liquid was light yellow, in which solid material formation was not observed.

Gas chromatography for the reaction liquid as described in Example 1 indicated that a conversion rate of 2-(methylamino)ethanol was 86%, a DMI yield was 73%, and an yield of a byproduct 1,4-dimethylpiperadine was 6%.

The reaction liquid was distilled in vacuo to give 30.9 g of 1,3-dimethyl-2-imidazolidinone whose purity was 99%.

Comparative Example 13

Using the autoclave described in Comparative Example 1, the materials were placed and reacted as described in Example 13. After the reaction, there were observed floating black solid materials. The liquid was filtered as described in Comparative Example 1 to give a brown filtrate. The dry weight of the black solids was 1.65 g.

Gas chromatography for the filtrate indicated that a conversion rate of 2-(methylamino)ethanol was 85%, a DMI yield was 67%, and an yield of a byproduct 1,4-dimethylpiperadine was 11%.

The reaction liquid was distilled in vacuo to give 28.1 g of 1,3-dimethyl-2-imidazolidinone whose purity was 99%.

EXAMPLE 14

In the autoclave described in Example 1 were placed 22.5 g of 2-(methylamino)ethanol (0.3 mol), 105.7 g of 1,3-dimethylurea (1.2 mol) and 54.1 g of ion exchange water (3.0 mol). After replacing the gas phase with nitrogen, 52.8 g of carbon dioxide (1.2 mol) was charged in the reaction system. Then, while externally heating the autoclave, these materials were reacted under stirring at an internal temperature of 200° C. for 8 hours. After the reaction, the reaction liquid was light yellow, in which solid material formation was not observed.

Gas chromatography for the reaction liquid as described in Example 1 indicated that a conversion rate of 2-(methylamino)ethanol was 97%, a DMI yield was 86%, and an yield of a byproduct 1,4-dimethylpiperadine was 5%.

Comparative Example 14

Using the autoclave described in Comparative Example 1, the materials were placed and reacted as described in Example 14. After the reaction, there were observed floating black solid materials. The liquid was filtered as described in Comparative Example 1 to give a brown filtrate. The dry weight of the black solids was 1.77 g.

Gas chromatography for the filtrate indicated that a inversion rate of 2-(methylamino)ethanol was 97%, a DMI yield was 78%, and an yield of a byproduct 1,4-dimethylpiperadine was 14%.

EXAMPLE 15

The autoclave described in Example 1 was heated 300° C. in the air, to form an oxide film over the inner surface of the autoclave. In the autoclave were placed 30.0 g of 2-(methylamino)ethanol (0.4 mol), 84.9 g of methylcarbamate methylamine salt (0.8 mol) and 18.0 g of ion exchange water (1.0 mol). After replacing the gas phase with nitrogen, 66.0 g of carbon dioxide (1.5 mol) was charged. Then, while externally heating the autoclave, these materials were reacted under stirring at an internal temperature of 210° C. for 6 hours. After the reaction, the reaction liquid was light yellow, in which solid material formation was not observed.

Gas chromatography for the reaction liquid as described in Example 1 indicated that a conversion rate of 2-(methylamino)ethanol was 98%, a DMI yield was 77%, and an yield of a byproduct 1,4-dimethylpiperadine was 9%.

Comparative Example 15

Using the autoclave described in Comparative Example 1, the materials were placed and reacted as described in Example 15. After the reaction, there were observed floating black solid materials. The liquid was filtered as described in Comparative Example 1 to give a brown filtrate. The dry weight of the black solids was 1.88 g.

Gas chromatography for the filtrate indicated that a conversion rate of 2-(methylamino)ethanol was 98%, a DMI yield was 67%, and an yield of a byproduct 1,4-dimethylpiperadine was 18%.

EXAMPLE 16

A cylindrical vessel made of pure zirconium was placed in the autoclave described in Comparative Example 1. In the cylindrical vessel were placed 15.0 g of 2-(methylamino) ethanol (0.2 mol), 88.1 g of 1,3-dimethylurea (1.0 mol) and 36.0 g of ion exchange water (2.0 mol). After replacing the gas phase with nitrogen, 44.0 g of carbon dioxide (1.0 mol) was charged. Then, while externally heating the autoclave, these materials were reacted under stirring at an internal temperature of 200° C. for 6 hours. After the reaction, the reaction liquid was light yellow, in which solid material formation was not observed.

Gas chromatography for the reaction liquid as described in Example 1 indicated that a conversion rate of 2-(methylamino)ethanol was 98%, a DMI yield was 88%, and an yield of a byproduct 1,4-dimethylpiperadine was 4%.

Comparative Example 16

Using the autoclave described in Comparative Example 1, the materials were placed and reacted as described in Example 16. After the reaction, there were observed floating black solid materials. The liquid was filtered as described in Comparative Example 1 to give a brown filtrate. The dry weight of the black solids was 1.60 g.

Gas chromatography for the filtrate indicated that a conversion rate of 2-(methylamino)ethanol was 99%, a DMI yield was 79%, and an yield of a byproduct 1,4-dimethylpiperadine was 10%.

EXAMPLE 17

In the autoclave described in Example 1 were placed 30.0 g of 2-(methylamino)ethanol (0.4 mol), 106.1 g of methylcarbamate methylamine salt (1.0 mol) and 22.8 g of DMI. After replacing the gas phase with nitrogen, 52.8 g of carbon dioxide (1.2 mol) was charged. Then, while externally heating the autoclave, these materials were reacted under stirring at an internal temperature of 200° C. for 6 hours. After the reaction, the reaction liquid was light yellow, in which solid material formation was not observed.

Gas chromatography for the reaction liquid as described in Example 1 indicated that a conversion rate of 2-(methylamino)ethanol was 86%, an yield of DMI formed against 2-(methylamino)ethanol charged was 72%, and an yield of a byproduct 1,4-dimethylpiperadine was 5%.

Comparative Example 17

Using the autoclave described in Example 17, a reaction was conducted as described in Example 17, except that DMI was replaced with 22.8 g of methanol.

After the reaction, the reaction liquid was brown, in which solid material formation was not observed.

Gas chromatography for the reaction liquid as described in Example 1 indicated that a conversion rate of 2-(methylamino)ethanol was 73%, a DMI yield was 58%, and an yield of a byproduct 1,4-dimethylpiperadine was 8%.

EXAMPLE 18

In the autoclave described in Example 1 was placed 24.8 g of ethylene glycol (0.4 mol). After replacing the gas phase with nitrogen, 74.6 g of monomethylamine (2.4 mol) and 52.8 g of carbon dioxide (1.2 mol) were charged. Then, while externally heating the autoclave, these materials were reacted under stirring at an internal temperature of 220° C. for 24 hours. After the reaction, the reaction liquid was light yellow, in which solid material formation was not observed.

Gas chromatography for the reaction liquid as described in Example 1 indicated that a conversion rate of ethylene glycol was 91%, an yield of DMI formed against ethylene glycol charged (hereinafter, referred to as a "DMI yield") was 70%, and a total yield of byproducts 1,4-dimethylpiperadine and 2-(methylamino)ethanol was 11%.

The reaction liquid was distilled in vacuo to give 30.6 g of 1,3-dimethyl-2-imidazolidinone whose purity was 99%.

Comparative Example 18

Using the autoclave described in Comparative Example 1, the materials were placed and reacted as described in Example 18. After the reaction, there were observed floating black solid materials. The liquid was filtered to give a brown filtrate. The dry weight of the black solids was 3.89 g.

Gas chromatography for the filtrate as described in Comparative Example 1 indicated that a conversion rate of ethylene glycol was 88%, a DMI yield was 66%, and a total yield of byproducts 1,4-dimethylpiperadine and 2-(methylamino)ethanol was 16%.

The filtrate was distilled in vacuo to give 28.1 g of 1,3-dimethyl-2-imidazolidinone whose purity was 99%.

EXAMPLE 19

In the autoclave described in Example 1 were placed 24.8 g of ethylene glycol (0.4 mol), 141.0 g of 1,3-dimethylurea (1.6 mol) and 28.8 g of ion exchange water (1.6 mol). After replacing the gas phase with nitrogen, a reaction was conducted as described in Example 18. After the reaction, the reaction liquid was light yellow, in which solid material formation was not observed.

Gas chromatography for the reaction liquid as described in Example 1 indicated that a conversion rate of ethylene glycol was 95%, a DMI yield was 74%, and a total yield of byproducts 1,4-dimethylpiperadine and 2-(methylamino)ethanol was 8%.

Comparative Example 19

Using the autoclave described in Comparative Example 1, the materials were placed and reacted as described in Example 19. After the reaction, there were observed floating black solid materials. The liquid was filtered as described in Comparative Example 1 to give a brown filtrate. The dry weight of the black solids was 4.01 g.

Gas chromatography for the filtrate as described in Comparative Example 1 indicated that a conversion rate of ethylene glycol was 91%, a DMI yield was 70%, and a total yield of byproducts 1,4-dimethylpiperadine and 2-(methylamino)ethanol was 13%.

EXAMPLE 20

In the autoclave described in Example 1 were placed 25.4 g of ethylene glycol (0.41 mol) and 56 g of ion exchange water (3.1 mol). After replacing the gas phase with nitrogen, 102.0 g of methylamine (3.3 mol) and 72.5 g of carbon dioxide (1.65 mol) were charged. Then, while externally heating the autoclave, these materials were reacted under stirring at an internal temperature of 250° C. for 15 hours. After the reaction, the reaction liquid was light yellow, in which solid material formation was not observed.

Gas chromatography for the reaction liquid as described in Example 1 indicated that a conversion rate of ethylene glycol was 91%, a DMI yield was 70%, and a total yield of byproducts 1,4-dimethylpiperadine and 2-(methylamino)ethanol was 5%.

Comparative Example 20

Using the autoclave described in Comparative Example 1, the materials were placed and reacted as described in Example 20. After the reaction, there were observed floating black solid materials. The liquid was filtered as described in Comparative Example 1 to give a brown filtrate. The dry weight of the black solids was 4.32 g.

Gas chromatography for the filtrate as described in Comparative Example 1 indicated that a conversion rate of ethylene glycol was 91%, a DMI yield was 64%, and a total yield of byproducts 1,4-dimethylpiperadine and 2-(methylamino)ethanol was 8%.

EXAMPLE 21

In a 80 mL (inner volume) autoclave made of SUS-316L which is equipped with a cylindrical vessel, a stirring rod and stirring blades, which are made of Ti—0.15Pd, were placed 5.0 g of ethylene glycol (0.08 mol), 42.4 g of methylcarbamate methylamine salt (0.40 mol) and 2.9 g of ion exchange water (0.16 mol), and the gas phase was replaced with nitrogen. Then, while externally heating the autoclave, these materials were reacted under stirring at an internal temperature of 240° C. for 18 hours. After the reaction, the reaction liquid was light yellow, in which solid material formation was not observed.

Gas chromatography for the reaction liquid as described in Example 1 indicated that a conversion rate of ethylene glycol was 93%, a DMI yield was 73%, and a total yield of byproducts, 1,4-dimethylpiperadine and 2-(methylamino)ethanol was 6%.

Comparative Example 21

Using a 80 mL (inner volume) autoclave made of SUS-316L, the materials were placed and reacted as described in Example 21. After the reaction, there were observed floating black solid materials. The liquid was filtered as described in Comparative Example 1 to give a brown filtrate. The dry weight of the black solids was 0.66 g.

Gas chromatography for the filtrate as described in Comparative Example 1 indicated that a conversion rate of ethylene glycol was 90%, a DMI yield was 71%, and a total yield of byproducts, 1,4-dimethylpiperadine and 2-(methylamino)ethanol was 8%.

EXAMPLE 22

In a 80 mL (inner volume) autoclave made of SUS-316L which is equipped with a cylindrical vessel, a stirring rod and stirring blades, which are made of Ti—6Al—4V, were placed 6.1 g of 1,2-propane diol (0.08 mol), 34.0 g of methylcarbamate methylamine salt (0.32 mol) and 4.3 g of ion exchange water (0.24 mol), and the gas phase was replaced with nitrogen. Then, while externally heating the autoclave, these materials were reacted under stirring at an internal temperature of 250° C. for 12 hours. After the reaction, the reaction liquid was light yellow, in which solid material formation was not observed.

Gas chromatography for the reaction liquid as described in Example 1 indicated that a conversion rate of 1,2-propane diol was 66%, an yield of 1,3,4-trimethyl-2-imidazolidinone formed against 1,2-propane diol charged was 48%, and a total yield of byproducts, 1,2,4-trimethylpiperadine and 1-methylamino-2-propanol was 7%.

Comparative Example 22

Using a 80 mL (inner volume) autoclave made of SUS-316L, the materials were placed and reacted as described in Example 22. After the reaction, there were observed floating black solid materials. The liquid was filtered as described in Comparative Example 1 to give a brown filtrate. The dry weight of the black solids was 0.51 g.

Gas chromatography for the filtrate as described in Comparative Example 1 indicated that a conversion rate of 1,2-propane diol was 64%, an yield of 1,3,4-trimethyl-2-imidazolidinone formed against 1,2-propane diol charged was 45%, and a total yield of byproducts, 1,2,4-trimethylpiperadine and 1-methylamino-2-propanol was 9%.

EXAMPLE 23

In the autoclave described in Example 1 were placed 24.8 g of ethylene glycol (0.4 mol), 127.3 g of methylcarbamate methylamine salt (1.2 mol) and 54.1 g of ion exchange water (3.0 mol), and the gas phase was replaced with nitrogen. Then, while externally heating the autoclave, these materials were reacted under stirring at an internal temperature of 210° C. for 20 hours. After the reaction, the reaction liquid was light yellow, in which solid material formation was not observed.

Gas chromatography for the reaction liquid indicated that a conversion rate of ethylene glycol was 43%, a DMI yield was 32%, and a total yield of byproducts 1,4-dimethylpiperadine and 2-(methylamino)ethanol was 6%.

The reaction liquid was distilled in vacuo to give 2.8 g of 1,3-dimethyl-2-imidazolidinone whose purity was 9%.

Comparative Example 23

Using the autoclave described in Comparative Example 1, the materials were placed and reacted as described in Example 23. After the reaction, there were observed floating black solid materials. The liquid was filtered to give a brown filtrate. The dry weight of the black solids was 2.20 g.

Gas chromatography for the filtrate as described in Comparative Example 1 indicated that a conversion rate of ethylene glycol was 43%, a DMI yield was 28%, and a total yield of byproducts 1,4-dimethylpiperadine and 2-(methylamino)ethanol was 8%.

The filtrate was distilled in vacuo to give 12.1 g of 1,3-dimethyl-2-imidazolidinone whose purity was 99%.

EXAMPLE 24

In the autoclave described in Example 1 were placed materials as described in Example 25, and then 52.8 g of carbon dioxide (1.2 mol) was charged. Then, while externally heating the autoclave, these materials were reacted under stirring at an internal temperature of 210° C. for 20 hours. After the reaction, the reaction liquid was light yellow, in which solid material formation was not observed.

Gas chromatography for the reaction liquid as described in Example 1 indicated that a conversion rate of ethylene glycol was 83%, an yield of DMI was 66%, and a total yield of byproducts including 1,4-dimethylpiperadine (hereinafter, referred to as a "byproduct yield") was 8%.

The reaction liquid was distilled in vacuo to give 28.5 g of 1,3-dimethyl-2-imidazolidinone whose purity was 99%.

Comparative Example 24

Using the autoclave described in Comparative Example 1, the materials were placed and reacted as described in Example 24. After the reaction, there were observed floating black solid materials. The liquid was filtered to give a brown filtrate. The dry weight of the black solids was 2.11 g.

Gas chromatography for the filtrate as described in Comparative Example 1 indicated that a conversion rate of ethylene glycol was 85%, a DMI yield was 62%, and a total yield of byproducts 1,4-dimethylpiperadine and 2-(methylamino)ethanol was 12%.

The filtrate was distilled in vacuo to give 26.3 g of 1,3-dimethyl-2-imidazolidinone whose purity was 99%.

EXAMPLE 25

In the autoclave described in Example 1 were placed 18.6 g of ethylene glycol (0.3 mol), 132.2 g of 1,3-dimethylurea (1.5 mol) and 27.0 g of ion exchange water (1.5 mol). After replacing the gas phase with nitrogen, 66.0 g of carbon dioxide (1.5 mol) was charged. Then, while externally heating the autoclave, these materials were reacted under stirring at an internal temperature of 200° C. for 30 hours. After the reaction, the reaction liquid was light yellow, in which solid material formation was not observed.

Gas chromatography for the reaction liquid indicated that a conversion rate of ethylene glycol was 78%, a DMI yield was 68%, and a total yield of byproducts 1,4-dimethylpiperadine and 2-(methylamino)ethanol was 7%.

Comparative Example 25

Using the autoclave described in Comparative Example 1, the materials were placed and reacted as described in Example 25. After the reaction, there were observed floating black solid materials. The liquid was filtered as described in Comparative Example 1 to give a brown filtrate. The dry weight of the black solids was 1.93 g.

Gas chromatography for the filtrate as described in Comparative Example 1 indicated that a conversion rate of ethylene glycol was 79%, a DMI yield was 65%, and a total yield of byproducts 1,4-dimethylpiperadine and 2-(methylamino)ethanol was 11%.

EXAMPLE 26

A cylindrical vessel made of zirconium was placed in the autoclave described in Comparative Example 1. In the cylindrical vessel were placed 24.8 g of ethylene glycol (0.4 mol), 105.7 g of 1,3-dimethylurea (1.2 mol) and 21.6 g of ion exchange water (1.2 mol). After replacing the gas phase with nitrogen, 66.0 g of carbon dioxide (1.5 mol) was charged. Then, while externally heating the autoclave, these materials were reacted under stirring at an internal temperature of 200° C. for 30 hours. After the reaction, the reaction liquid was light yellow, in which solid material formation was not observed.

Gas chromatography for the reaction liquid as described in Example 1 indicated that a conversion rate of ethylene glycol was 74%, a DMI yield was 60%, and a total yield of byproducts 1,4-dimethylpiperadine and 2-(methylamino) ethanol was 5%.

Comparative Example 26

Using the autoclave described in Comparative Example 1, the materials were placed and reacted as described in Example 26. After the reaction, there were observed floating black solid materials. The liquid was filtered as described in Comparative Example 1 to give a brown filtrate. The dry weight of the black solids was 1.59 g.

Gas chromatography for the filtrate as described in Comparative Example 1 indicated that a conversion rate of ethylene glycol was 71%, a DMI yield was 55%, and a total yield of byproducts 1,4-dimethylpiperadine and 2-methylamino)ethanol was 7%.

What is claimed is:

1. A process for manufacturing 1,3-dialkyl-2-imidazolidinone represented by formula (1):

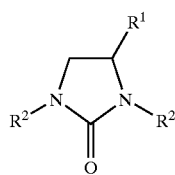
(1)

wherein $R^1$ is hydrogen or $C_1$–$C_6$ alkyl and $R^2$ is $C_1$–$C_6$ alkyl, containing 50 ppm by weight or less of 1-alkoxyalkyl-3-alkyl-2-imidazolidinone represented by formula (2):

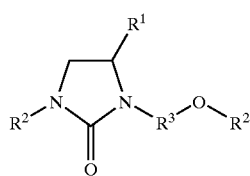
(2)

wherein $R^1$ and $R^2$ are as defined above; and $R^3$ is $C_1$–$C_6$ alkylene; or formula (3):

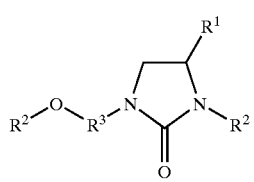
(3)

wherein $R^1$, $R^2$ and $R^3$ are as defined above; comprising heating at 50° C. or higher N-alkylmonoethanolamine represented by formula (9):

(9)

wherein $R^1$ and $R^2$ are as defined above; with at least one of:
i) carbon dioxide and monoalkylamine represented by formula (6):

$R^2NH_2$ (6)

wherein $R^2$ is as defined above,
ii) alkylcarbamate alkylamine salt represented by formula (7):

$R^2NHCOOH.R^2NH_2$ (7)

wherein $R^2$ is as defined above, and
iii) 1,3-dialkylurea represented by formula (8):

$R^2NHCONHR^2$ (8)

wherein $R^2$ is as defined above; in a reactor having a surface that contacts at least a part of at least one of the N-alkylmonoethanolamine, the at least one of i), ii) and iii), and the 1,3-dialkyl-2-imidazolidinone is made of (I) a material comprising at least one of titanium, zirconium, titanium oxide or zirconium oxide or (II) inorganic glass.

2. A process for manufacturing 1,3-dialkyl-2-imidazolidinone as claimed in claim 1 containing 0.5 wt % or less of N-alkylformamide represented by formula (4):

$R^2NHCHO$ (4)

wherein $R^2$ is $C_1$–$C_6$ alkyl.

3. A process for manufacturing 1,3-dialkyl-2-imidazolidinone represented by formula (1):

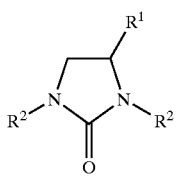
(1)

wherein $R^1$ is hydrogen or $C_1$–$C_6$ alkyl and $R^2$ is $C_1$–$C_6$ alkyl, containing 50 ppm by weight or less of 1-alkoxyalkyl-3-alkyl-2-imidazolidinone represented by formula (2):

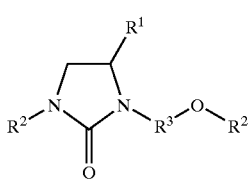
(2)

wherein $R^1$ and $R^2$ are as defined above; and $R^3$ is $C_1$–$C_6$ alkylene; or formula (3):

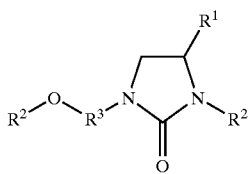
(3)

wherein $R^1$, $R^2$ and $R^3$ are as defined above; comprising heating at 50° C. or higher N-alkylmonoethanolamine represented by formula (9):

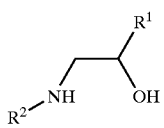
(9)

wherein $R^1$ and $R^2$ are as defined above, with at least one of: alkylcarbamate alkylamine salt represented by formula (7):

wherein $R^2$ is as defined above, and 1,3-dialkylurea represented by formula (8):

wherein $R^2$ is as defined above, in the presence of carbon dioxide, in a reactor having a surface that contacts at least a part of at least one of the N-alkylmonoethanolamine, at least one of the alkylcarbamate alkylamine salt and 1,3-dialkylurea, and the 1,3-dialkyl-2-imidazolidinone is made of (I) a material comprising at least one of titanium, zirconium, titanium oxide or zirconium oxide or (II) inorganic glass.

4. A process for manufacturing 1,3-dialkyl-2-imidazolidinone as claimed in claim 3 containing 0.5 wt % or less of N-alkylformamide represented by formula (4):

wherein $R^2$ is $C_1$–$C_6$ alkyl.

5. A process as claimed in claim 1 for manufacturing 1,3-dimethyl-2-imidazolidinone, where N-alkylmonoethanolamine is 2-(methylamino)ethanol; monoalkylamine is monomethylamine; alkylcarbamate alkylamine salt is methylcarbamate methylamine salt; and 1,3-dialkylurea is 1,3-dimethylurea and wherein the 1,3-dimethyl-2-imidazolidinone contains 50 ppm by weight or less of 1-methoxymethyl-3-methyl-2-imidazolidinone.

6. A process as claimed in claim 2 for manufacturing 1,3-dimethyl-2-imidazolidinone, where N-alkylmonoethanolamine is 2-(methylamino)ethanol; monoalkylamine is monomethylamine; alkylcarbamate alkylamine salt is methylcarbamate methylamine salt; and 1,3-dialkylurea is 1,3-dimethylurea and wherein the 1,3-dimethyl-2-imidazolidinone contains 50 ppm by weight or less of 1-methoxymethyl-3-methyl-2-imidazolidinone.

7. A process as claimed in claim 3 for manufacturing 1,3-dimethyl-2-imidazolidinone, where N-alkylmonoethanolamine is 2-(methylamino)ethanol; alkylcarbamate alkylamine salt is methylcarbamate methylamine salt; and 1,3-dialkylurea is 1,3-dimethylurea and wherein the 1,3-dimethyl-2-imidazolidinone contains 50 ppm by weight or less of 1-methoxymethyl-3-methyl-2-imidazolidinone.

8. A process as claimed in claim 4 for manufacturing 1,3-dimethyl-2-imidazolidinone, where N-alkylmonoethanolamine is 2-(methylamino)ethanol; alkylcarbamate alkylamine salt is methylcarbamate methylamine salt; and 1,3-dialkylurea is 1,3-dimethylurea and wherein the 1,3-dimethyl-2-imidazolidinone contains 50 ppm by weight or less of 1-methoxymethyl-3-methyl-2-imidazolidinone.

9. A process as claimed in claim 1 where the reactor is wholly made of a material comprising at least one of titanium, zirconium, titanium oxide and zirconium oxide or at least part of the inside wall is coated with a material comprising at least one of titanium, zirconium, titanium oxide and zirconium oxide.

10. A process as claimed in claim 2 where the reactor is wholly made of a material comprising at least one of titanium, zirconium, titanium oxide and zirconium oxide or at least part of the inside wall is coated with a material comprising at least one of titanium, zirconium, titanium oxide and zirconium oxide.

11. A process as claimed in claim 9 where at least part of the inside wall of the reactor is coated with a metal comprising titanium or zirconium that is clad or baked on the inside wall of the reactor.

12. A process as claimed in claim 10 where at least part of the inside wall of the reactor is coated with a metal comprising titanium or zirconium that is clad or baked on the inside wall of the reactor.

13. A process as claimed in claim 9 where at least part of the inside wall of the reactor is coated with an oxide of a metal comprising titanium or zirconium formed by oxidation on the inside wall of the reactor.

14. A process as claimed in claim 10 where at least part of the inside wall of the reactor is coated with an oxide of a metal comprising titanium or zirconium formed by oxidation on the inside wall of the reactor.

15. A process as claimed in claim 9 where at least part of the inside wall of the reactor is coated with an oxide of a metal comprising titanium or zirconium formed by thermal decomposition on the inside wall of the reactor.

16. A process as claimed in claim 10 where at least part of the inside wall of the reactor is coated with an oxide of a metal comprising titanium or zirconium formed by thermal decomposition on the inside wall of the reactor.

17. A process as claimed in claim 1 where the metal comprising titanium or zirconium is selected from the group consisting of industrial pure titanium, corrosive resistant titanium-alloy and pure zirconium.

18. A process as claimed in claim 2 where the metal comprising titanium or zirconium is selected from the group consisting of industrial pure titanium, corrosive resistant titanium-alloy and pure zirconium.

19. A process as claimed in claim 1 where the reaction is conducted at 100 to 300° C.

20. A process as claimed in claim 2 where the reaction is conducted at 100 to 300° C.

21. A process as claimed in claim 1 where 1,3-dialkyl-2-imidazolidinone represented by formula (1):

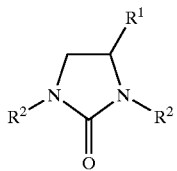

(1)

wherein $R^1$ is hydrogen or $C_1$–$C_6$ alkyl and $R^2$ is $C_1$–$C_6$ alkyl, or water is used as a solvent.

22. A process as claimed in claim 2 where 1,3-dialkyl-2-imidazolidinone represented by formula (1):

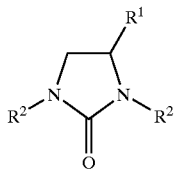

(1)

wherein $R^1$ is hydrogen or $C_1$–$C_6$ alkyl and $R^2$ is $C_1$–$C_6$ alkyl, or water is used as a solvent.

23. A process as claimed in claim 3 where the reactor is wholly made of a material comprising at least one of titanium, zirconium, titanium oxide and zirconium oxide or at least part of the inside wall is coated with a material comprising at least one of titanium, zirconium, titanium oxide and zirconium oxide.

24. A process as claimed in claim 4 where the reactor is wholly made of a material comprising at least one of titanium, zirconium, titanium oxide and zirconium oxide or at least part of the inside wall is coated with a material comprising at least one of titanium, zirconium, titanium oxide and zirconium oxide.

25. A process as claimed in claim 23 where at least part of the inside wall of the reactor is coated with a metal comprising titanium or zirconium that is clad or baked on the inside wall of the reactor.

26. A process as claimed in claim 24 where at least part of the inside wall of the reactor is coated with a metal comprising titanium or zirconium that is clad or baked on the inside wall of the reactor.

27. A process as claimed in claim 23 where at least part of the inside wall of the reactor is coated with an oxide of a metal comprising titanium or zirconium formed by oxidation on the inside wall of the reactor.

28. A process as claimed in claim 24 where at least part of the inside wall of the reactor is coated with an oxide of a metal comprising titanium or zirconium formed by oxidation on the inside wall of the reactor.

29. A process as claimed in claim 23 where at least part of the inside wall of the reactor is coated with an oxide of a metal comprising titanium or zirconium formed by thermal decomposition on the inside wall of the reactor.

30. A process as claimed in claim 24 where at least part of the inside wall of the reactor is coated with an oxide of a metal comprising titanium or zirconium formed by thermal decomposition on the inside wall of the reactor.

31. A process as claimed in claim 3 where the titanium or zirconium is selected from the group consisting of industrial pure titanium, corrosive resistant titanium-alloy and pure zirconium.

32. A process as claimed in claim 4 where the titanium or zirconium is selected from the group consisting of industrial pure titanium, corrosive resistant titanium-alloy and pure zirconium.

33. A process as claimed in claim 3 where the reaction is conducted at 100 to 300° C.

34. A process as claimed in claim 4 where the reaction is conducted at 100 to 300° C.

35. A process as claimed in claim 3 where 1,3-dialkyl-2-imidazolidinone represented by formula (1):

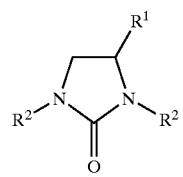

(1)

wherein $R^1$ is hydrogen or $C_1$–$C_6$ alkyl and $R^2$ is $C_1$–$C_6$ alkyl, or water is used as a solvent.

36. A process as claimed in claim 4 where 1,3-dialkyl-2-imidazolidinone represented by formula (1):

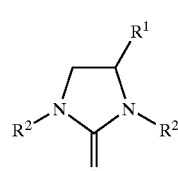

(1)

wherein $R^1$ is hydrogen or $C_1$–$C_6$ alkyl and $R^2$ is $C_1$–$C_6$ alkyl, or water is used as a solvent.

37. A process as claimed in claim 1 for manufacturing 1,3-dimethyl-2-imidazolidinone, where N-alkylmonoethanolamine is 2-(methylamino)ethanol; monoalkylamine is monomethylamine; alkylcarbamate alkylamine salt is methylcarbamate methylamine salt; and 1,3-dialkylurea is 1,3-dimethylurea and wherein the 1,3-dimethyl-2-imidazolidinone contains 0.5 wt % or less of N-methylformamide.

38. A process as claimed in claim 2 for manufacturing 1,3-dimethyl-2-imidazolidinone, where N-alkylmonoethanolamine is 2-(methylamino)ethanol; monoalkylamine is monomethylamine; alkylcarbamate alkylamine salt is methylcarbamate methylamine salt; and 1,3-dialkylurea is 1,3-dimethylurea and wherein the 1,3-dimethyl-2-imidazolidinone contains 0.5 wt % or less of N-methylformamide.

39. A process as claimed in claim 3 for manufacturing 1,3-dimethyl-2-imidazolidinone, where N-alkylmonoethanolamine is 2-(methylamino)ethanol; alkylcarbamate alkylamine salt is methylcarbamate methylamine salt; and 1,3-dialkylurea is 1,3-dimethylurea and wherein the 1,3-dimethyl-2-imidazolidinone contains 0.5 wt % or less of N-methylformamide.

40. A process as claimed in claim 4 for manufacturing 1,3-dimethyl-2-imidazolidinone, where N-alkylmonoethanolamine is 2-(methylamino)ethanol; alkylcarbamate alkylamine salt is methylcarbamate methylamine salt; and 1,3-dialkylurea is 1,3-dimethylurea and wherein the 1,3-dimethyl-2-imidazolidinone contains 0.5 wt % or less of N-methylformamide.

* * * * *